United States Patent
Serban et al.

(10) Patent No.: US 8,679,320 B2
(45) Date of Patent: *Mar. 25, 2014

(54) PROCESS FOR INCREASING BENZENE AND TOLUENE PRODUCTION

(75) Inventors: Manuela Serban, Glenview, IL (US); Antoine Negiz, Wilmette, IL (US); Kurt M. VandenBussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/428,005

(22) Filed: Mar. 23, 2012

(65) Prior Publication Data

US 2012/0273392 A1    Nov. 1, 2012

Related U.S. Application Data

(60) Provisional application No. 61/480,765, filed on Apr. 29, 2011.

(51) Int. Cl.
*C10G 59/02* (2006.01)

(52) U.S. Cl.
USPC .............. 208/63; 208/64; 208/62; 585/319

(58) Field of Classification Search
USPC .............................. 208/63, 64, 62; 585/319
See application file for complete search history.

(56) References Cited

U.S. PATENT DOCUMENTS

| | | | | |
|---|---|---|---|---|
| 2,324,165 A | * | 7/1943 | Layng et al. | 208/79 |
| 2,866,745 A | * | 12/1958 | Heinemann | 208/79 |
| 4,401,554 A | * | 8/1983 | Choi et al. | 208/64 |
| 4,897,177 A | * | 1/1990 | Nadler | 208/79 |

OTHER PUBLICATIONS

U.S. Appl. No. 13/416,513, filed Mar. 9, 2012, Serban.
U.S. Appl. No. 13/416,702, filed Mar. 9, 2012, Gajda.
U.S. Appl. No. 13/417,181, filed Mar. 9, 2012, Gajda.
U.S. Appl. No. 13/417,200, filed Mar. 9, 2012, Wegerer.
U.S. Appl. No. 13/417,202, filed Mar. 9, 2012, Gajda.
U.S. Appl. No. 13/417,203, filed Mar. 10, 2012, Gajda.
U.S. Appl. No. 13/440,487, filed Apr. 5, 2012, Moser.
U.S. Appl. No. 13/440,527, filed Apr. 5, 2012, Moser.
U.S. Appl. No. 13/440,381, filed Apr. 5, 2012, Moser.
U.S. Appl. No. 13/416,577, filed Mar. 9, 2012, Negiz.
U.S. Appl. No. 13/416,604, filed Mar. 9, 2012, Serban.
U.S. Appl. No. 13/327,164, filed Dec. 15, 2011, Moser.
U.S. Appl. No. 13/327,200, filed Dec. 15, 2011, Moser.
U.S. Appl. No. 13/327,143, filed Dec. 15, 2011, Moser.
U.S. Appl. No. 13/327,212, filed Dec. 15, 2011, Moser.
U.S. Appl. No. 13/327,220, filed Dec. 15, 2011, Moser.
U.S. Appl. No. 13/327,185, filed Dec. 15, 2011, Serban.
U.S. Appl. No. 13/327,178, filed Dec. 15, 2011, Serban.
U.S. Appl. No. 13/327,170, filed Dec. 15, 2011, Serban.
U.S. Appl. No. 13/327,192, filed Dec. 15, 2011, Serban.

* cited by examiner

*Primary Examiner* — Thuan D Dang
(74) *Attorney, Agent, or Firm* — Arthur E Gooding

(57) ABSTRACT

A process for reforming a hydrocarbon stream is presented. The process involves splitting a naphtha feedstream to at least two feedstreams and passing each feedstream to separation reformers. The reformers are operated under different conditions to utilize the differences in the reaction properties of the different hydrocarbon components. The process utilizes a common catalyst, and common downstream processes for recovering the desired aromatic compounds generated.

7 Claims, 3 Drawing Sheets

PROCESS FOR INCREASING BENZENE AND TOLUENE PRODUCTION

CROSS-REFERENCE TO RELATED APPLICATION

This application claims priority from U.S. Provisional Application No. 61/480,765, filed Apr. 29, 2011, the contents of which are hereby incorporated by reference in its entirety.

FIELD OF THE INVENTION

The present invention relates to the process of enhancing the production of aromatic compounds. In particular the improvement and enhancement of aromatic compounds such as benzene, toluene and xylenes from a naphtha feedstream.

BACKGROUND OF THE INVENTION

The reforming of petroleum raw materials is an important process for producing useful products. One important process is the separation and upgrading of hydrocarbons for a motor fuel, such as producing a naphtha feedstream and upgrading the octane value of the naphtha in the production of gasoline. However, hydrocarbon feedstreams from a raw petroleum source include the production of useful chemical precursors for use in the production of plastics, detergents and other products.

The upgrading of gasoline is an important process, and improvements for the conversion of naphtha feedstreams to increase the octane number have been presented in U.S. Pat. Nos. 3,729,409, 3,753,891, 3,767,568, 4,839,024, 4,882,040 and 5,242,576. These processes involve a variety of means to enhance octane number, and particularly for enhancing the aromatic content of gasoline.

Processes include splitting feeds and operating several reformers using different catalysts, such as a monometallic catalyst or a non-acidic catalyst for lower boiling point hydrocarbons and bi-metallic catalysts for higher boiling point hydrocarbons. Other improvements include new catalysts, as presented in U.S. Pat. Nos. 4,677,094, 6,809,061 and 7,799,729. However, there are limits to the methods and catalysts presented in these patents, and which can entail significant increases in costs.

SUMMARY OF THE INVENTION

A process for improving the yields of aromatics from a hydrocarbon feedstream is presented. The process includes passing the feedstream to a reformer, to create a reformer effluent stream. The reformer effluent stream is passed to a fractionator, which is either a debutanizer, or a depentanizer, to separate out a light gas stream comprising C4 and lighter gases, or C5 and lighter gases. The fractionator generates a bottoms stream comprising aromatics and the bottoms stream is passed to a reformate splitter. The reformate splitter is operated to generate an overhead stream comprising C7 and lighter aromatics, and a bottoms stream comprising C8 and heavier aromatics. The reformate overhead stream is passed to an aromatics separation unit. The separation unit creates a purified aromatics product stream and a raffinate stream comprising non-aromatic hydrocarbons. The raffinate stream is passed to a second reformer, that is operated at a second set of operating conditions, and generates a second reformer effluent stream. The effluent stream is passed to the fractionator to pass the generated aromatics to the aromatics separation unit.

Other objects, advantages and applications of the present invention will become apparent to those skilled in the art from the following detailed description and drawings.

DETAILED DESCRIPTION OF THE INVENTION

The present invention is directed to improving the yields of aromatics from a hydrocarbon feedstream. In particular, the improvement is for a naphtha feedstream where the hydrocarbons are reformed to increase the yields of aromatics in the C6 to C8 range. The new process is designed to utilize a single catalyst, rather than a more expensive process that includes multiple catalysts.

The demand for aromatic compounds is increasing as the use of plastics and detergents increase. An important aspect of increasing the supply of aromatic compounds involves increasing the yields of aromatic compounds from current processes. Currently, naphtha boiling range hydrocarbons are processed with reformers to increase the aromatics content. This can be for upgrading octane numbers for gasoline, or for increasing the supply of benzene, toluene and xylenes. This is important for the production of plastics, and in particular plastic precursors such as paraxylene. Another important use of aromatics is the production of detergents.

Figure 1:
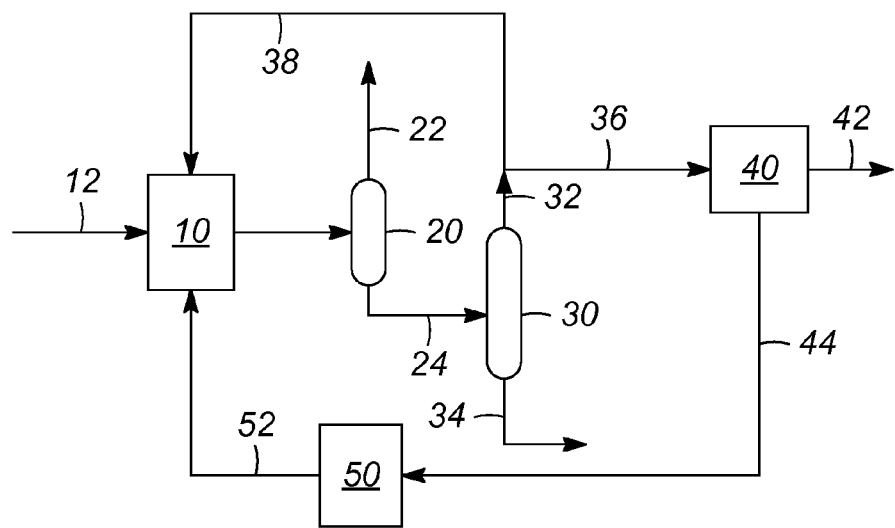
FIG. 1 is a schematic of a process for increasing aromatic yields from a reformer with a raffinate recycle.

The present invention involves the use of recycle and rearrangement of some of the equipment used in the process of reforming a naphtha feedstream. The process, as shown in FIG. 1, includes passing a naphtha feedstream 12 to a reformer 10, where a reformate stream 14 is generated. The reformate stream 14 is passed to a first fractionation unit 20, where a light overhead stream 22 and a bottoms stream 24 are created. The first fractionation unit 20 can be a debutanizer, or a depentanizer, and therefore the light overhead stream 24 comprises C4 and lighter hydrocarbons and gases, or C5 and lighter hydrocarbons and gases, respectively. The bottoms stream 24 is passed to a reformate splitter 30 where a reformate overhead stream 32 and a reformate bottoms stream 34 are generated. The reformate overhead stream 32 comprises C6 and C7 aromatic compounds, or benzene and toluene. The reformate bottoms stream 34 comprises C8 and heavier aromatic compounds. The reformate overhead stream 32 is passed to an aromatics extraction unit 40, to generate a purified aromatics stream 42 comprising C6 and C7 aromatic compounds, and a raffinate stream 44 comprising non-aromatic hydrocarbon compounds. The raffinate stream 44 is passed to the reformer 10.

The aromatics separation unit 40 can comprise different methods of separating aromatics from a hydrocarbon stream. One industry standard is the Sulfolane™ process, which is an extractive distillation process utilizing sulfolane to facilitate high purity extraction of aromatics. The Sulfolane™ process is well known to those skilled in the art.

The use of the Sulfolane™ process can leave residual amounts of sulfur compounds in the raffinate stream. The reformer catalyst is generally subject to poisoning by sulfur compounds and the feedstreams to the reformer will need to be treated for removal of sulfur. The process further comprises passing the raffinate stream 44 to a hydrotreater 50, where a hydrotreater effluent stream 52 with a reduced sulfur content is created. The hydrotreater effluent stream 52 is passed to the reformer 10.

The naphtha feedstream can contain some sulfur, and will need to be treated for sulfur removal. The naphtha feedstream 12 can be passed to the hydrotreater 50 prior to passing the naphtha feedstream 12 to the reformer 10. Where the naphtha feedstream 12 is treated in a hydrotreater 50, the same hydrotreater can be used for both the naphtha feedstream 12 and the raffinate stream 44.

In an alternate embodiment, the reformate overhead 32 is split into two portions, a first portion 36, and a second portion 38. The first portion 36 is passed to the aromatics extraction unit 40, and the second portion 38 is passed to the reformer 10. The passing of a portion of the reformate overhead 32 to the reformer 10 allows for control of the reaction residence time of the process stream in the reformer 10. The reforming reaction for lighter hydrocarbons, such as C6s, yields better results with shorter contact times between the C6s and the catalyst.

The processing of a mixture of hydrocarbons to generate aromatics can require a better understanding of the chemistry, which can lead to counter-intuitive results. When processing a hydrocarbon feedstream, the feedstream is separated to take advantage of differences in the chemistry of the different hydrocarbon components. It is important to understand the conversion of the different paraffinic compounds and naphthenic compounds to aromatics, in order to increase the yields in the conversion process. While it was assumed that smaller paraffins, such as C6s and C1s would convert more easily than heavier paraffins, such as C8s and heavier, it was found that the reverse is true. This leads to changes in the processing flow of the naphtha feedstock, such as a lower residence time for the naphtha feedstock in the reactor, and a recycle of the remaining hydrocarbons after recovering the desired aromatic compounds.

As presented herein, the reformer is a reactor that can comprise a plurality of reactor beds, and is intended to incorporate the use of multiple reactor beds within the scope of the invention. The reaction is endothermic and heat needs to be added to facilitate the reaction. The reformer can also include interbed heaters, wherein the process reheats catalyst and/or the process stream as the catalyst and process stream flow from one reactor bed to a sequential reactor bed within the reformer. A typical interbed heater is a fired heater that heats both the catalyst and the process stream as it passes from one reactor bed to another reactor bed. For highly endothermic reactions, the beds will tend to be smaller with the heaters returning the process stream and catalyst to a selected reactor bed inlet temperature.

A particular reforming reactor is one that performs a high temperature endothermic catalytic reaction for the cyclization and dehydrogenation of hydrocarbons. This reformer increases the aromatics content of a naphtha feedstream, and generates a hydrogen stream also. In particular, the production of benzene, toluene and xylenes.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

The reforming process is a common process in the refining of petroleum, and is usually used for increasing the amount of gasoline. The reforming process comprises mixing a stream of hydrogen and a hydrocarbon mixture and contacting the resulting stream with a reforming catalyst. The reforming reaction converts paraffins and naphthenes through dehydrogenation and cyclization to aromatics. The dehydrogenation of paraffins can yield olefins, and the dehydrocyclization of paraffins and olefins yields aromatics. The usual feedstock is a naphtha feedstock and generally has an initial boiling point of about 80° C. and an end boiling point of about 205° C. Normal operating pressures for a reformer are from 240 kPa to 580 kPa with a preferred pressure of around 450 kPa (50 psig). And the normal temperatures for operating the reformer is between 450° C. and 540° C. Generally, the reforming process is endothermic, and therefore the temperature in the reformer will drop relative to the inlet temperature. The operating temperature, therefore, is taken as the inlet temperature, and the interbed heaters used to raise the temperature of the catalyst and process stream will return the temperature to the inlet temperature before passing the catalyst and process stream to a subsequent reactor bed.

The recycling of the raffinate stream 44 allows for shorter contact times in the reactor, as well as increasing the reformer temperatures to temperatures greater than 560° C.

Figure 2:
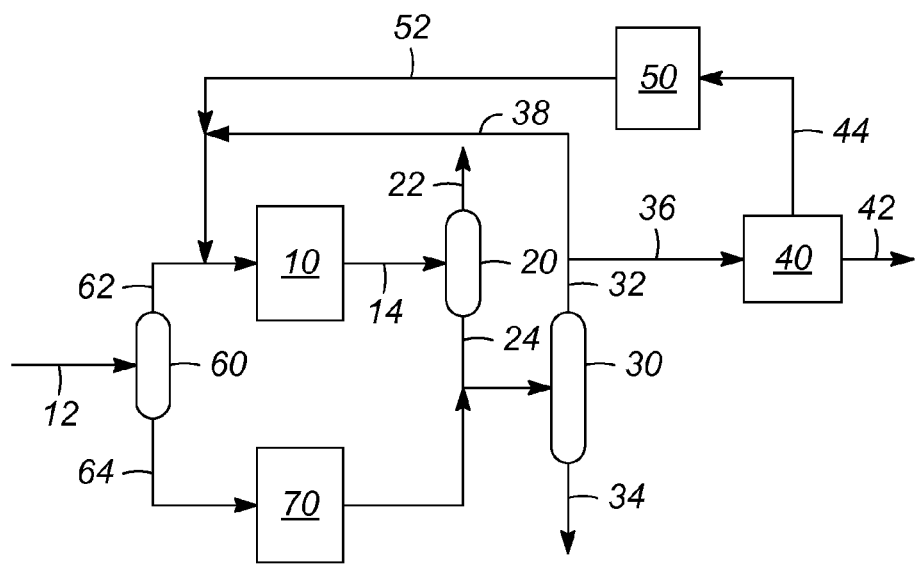
FIG. 2 is the first process for increasing aromatic yields from a naphtha feedstock with a raffinate recycle and adding a second reformer.

The process can further include the use of multiple reformers, wherein the reformers use different operating conditions, including different possible catalysts. One embodiment, as shown in FIG. 2, includes the passing of the naphtha feedstream 12 to a second fractionation unit 60 creating an overhead stream 62 comprising a light naphtha fraction, and a bottoms stream 64 comprising a heavy naphtha fraction. The light naphtha fraction can include C7 and lighter hydrocarbons or C6 and lighter hydrocarbons, and the heavy naphtha fraction can include C8 and heavier hydrocarbons or C7 and heavier hydrocarbons. The operational selection will depend on the quality of the feedstream 12 and other variables. The overhead stream 62 is passed to the reformer 10, and the bottoms stream 64 is passed to a second reformer 70, where a second reformate stream 72 is created. The second reformate stream 72 is passed to the reformate splitter 30.

When operating the process with a second reformer 70, the first reformer 10 is preferably operated at a higher temperature, where a preferred operation temperature is at least 540 C. and a more preferred operating temperature of at least 560 C. The second reformer 70 can be operated at as high a temperature as the first reformer 10. However, a preferred operation temperature for the second reformer is at a lower temperature, or a temperature less than 540 C. The second reformer will be receiving heavier paraffins and naphthenic compounds, and the operating conditions are for a less severe temperature, higher pressure, and longer contact times than the first reformer 10. The flow conditions include a WHSV in the range from 0.1 hr$^{-1}$ to 10 hr$^{-1}$, and a preferred WHSV in the range from 0.75 hr$^{-1}$ to 3 hf$^{-1}$.

Figure 3:
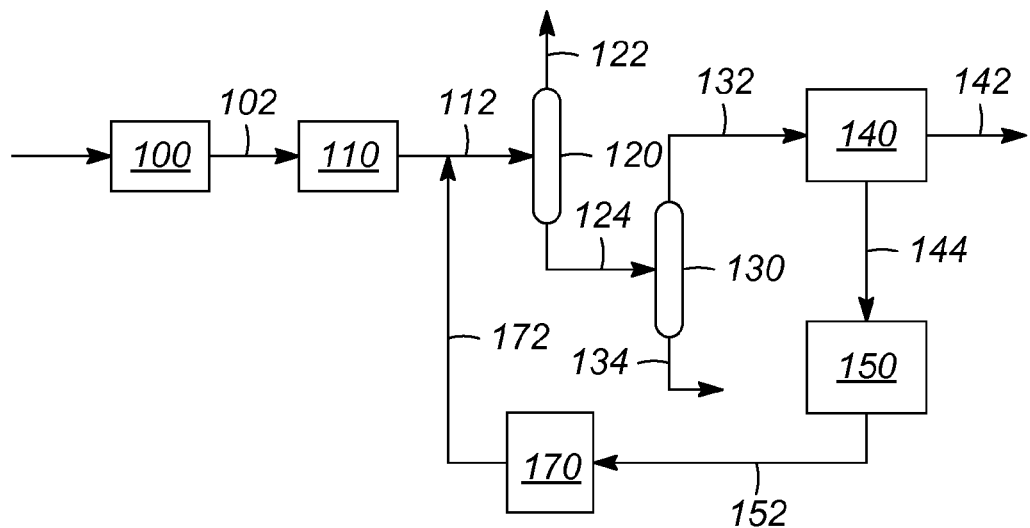
FIG. 3 is a second process for using a raffinate recycle with a downstream reformer.

The recycling of the raffinate stream can be performed in several processes. One process for increasing aromatics production from a naphtha feedstream is presented in FIG. 3. The naphtha feedstream 102 is passed to a first reformer 110, that is operated at a first set of reaction conditions, and generates a first reformer effluent stream 112. The effluent stream 112 is passed to a fractionator 120 to separate the effluent stream 112 into a light gas stream 122 and a bottoms stream 124. The light gas stream comprises C4 and lighter gases, or C5 and lighter gases, when the fractionator is a debutanizer or a depentanizer respectively. The bottoms stream 124 comprises aromatics and heavier hydrocarbon compounds.

The fractionator bottoms stream 124 is passed to a reformate splitter 130, where the bottoms stream 124 is split into an overhead stream 132 comprising lighter aromatics, and a bottoms stream 134 comprising heavier aromatics. The lighter aromatics are C6 to C8 aromatic compounds and preferably C6 and C7 aromatic compounds. The heavier aromatics include C9 and heavier aromatics. The reformate overhead stream 132 is passed to an aromatics extraction unit 140 to generate a purified aromatics product stream 142 and a raffinate stream 144. The raffinate stream 144 is passed to a second reformer 170, which is operated at a second set of reforming conditions, and generates a second reformer effluent stream 172. The second reformer effluent stream 172 is passed to the fractionator 120 to recover aromatics generated in the second reformer 170. The second reformer 170 in this process configuration is generally operated at higher temperatures.

The aromatics extraction unit 140 can impart some sulfur containing compounds to the raffinate stream 144. The reformer catalysts are sensitive to sulfur compounds, and the process can include a hydrotreater 150 for removing residual sulfur compounds. The raffinate stream is passed to the hydrotreater 150 to generate a reduced sulfur raffinate stream 152. The reduced sulfur raffinate stream 152 is passed to the second reformer 170, and the second reformer process stream 172 is passed to the fractionator 120.

The process can include passing the naphtha feedstream 102 to a hydrotreater 100 prior to passing the naphtha feedstream 102 to the first reformer 110. This generates a reduced sulfur naphtha feedstream 102. When a hydrotreater 100 is used for treating the naphtha feedstream 102, the raffinate stream 144 can be passed to the hydrotreater 100, with the hydrotreater effluent stream passed to the reformer 110.

Another embodiment of the process for recycling the raffinate stream includes splitting the feedstream to the reformers. The splitting of the feedstream to the reformers allows the processing of the different feeds to different reformers and using different catalysts in each of the reformers, as well as operating the different reformers under different conditions.

Reforming catalysts generally comprise a metal on a support. The support can include a porous material, such as an inorganic oxide or a molecular sieve, and a binder with a weight ratio from 1:99 to 99:1. The weight ratio is preferably from about 1:9 to about 9:1. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Porous materials and binders are known in the art and are not presented in detail here. The metals preferably are one or more Group VIII noble metals, and include platinum, iridium, rhodium, and palladium. Typically, the catalyst contains an amount of the metal from about 0.01% to about 2% by weight, based on the total weight of the catalyst. The catalyst can also include a promoter element from Group IIIA or Group IVA. These metals include gallium, germanium, indium, tin, thallium and lead.

When splitting the feed and using different catalysts, a feed comprising heavier hydrocarbon components will generally use a standard style reforming catalyst as described above. A lighter feed can use a low acid or non-acid catalyst. The low acid or non-acid catalyst can dehydrogenate naphthenes, and cyclize the lighter paraffins with minimal cracking.

Figure 4:
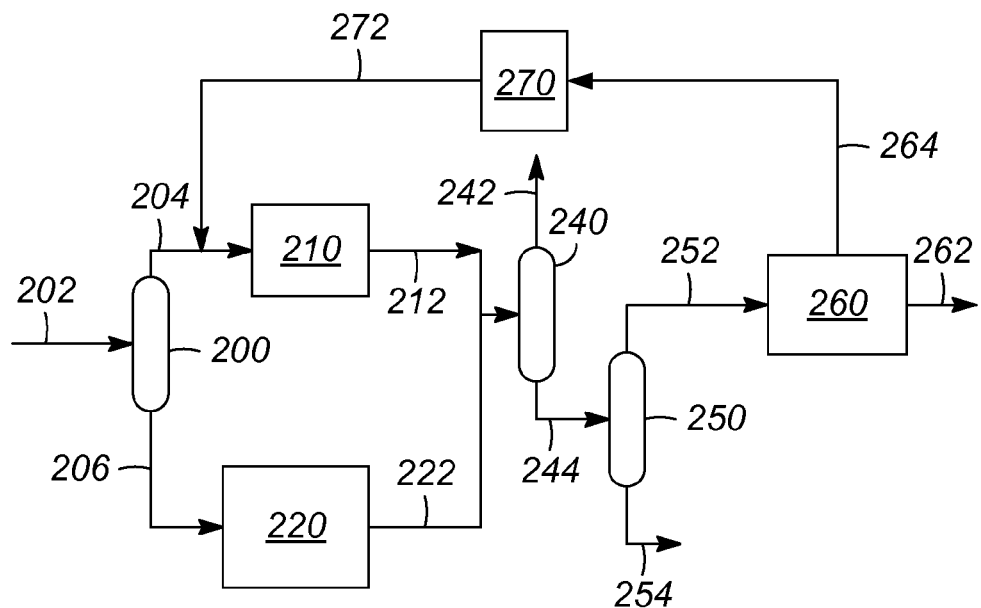
FIG. 4 is a third process using at least two reformers with raffinate recycle to the first reformer.

The process is as shown in FIG. 4, and includes passing a naphtha feedstream 202 to a first fractionation unit 200, to generate a first stream 204 having light hydrocarbons and a second stream 206 having heavier hydrocarbons. The first stream 204 is passed to a first reformer 210 and generates a first reformer effluent stream 212. The second stream 206 is passed to a second reformer 220 and generates a second reformer effluent stream 222. The first reformer effluent stream 212 and the second reformer effluent stream 222 are passed to a light hydrocarbon fractionation unit 240. The fractionation unit 240 separates out light gases, including light hydrocarbons in the C4-range, or C5-range, and passes them out as an overhead stream 242. The fractionation unit 240 also generates a bottoms stream 244 comprising reformate and passes the reformate to a reformate splitter 250. The reformate splitter 250 generates an overhead stream 252 comprising C6 and C7 aromatics, and a bottoms stream 254 comprising C8+ aromatics and heavier compounds. The reformate overhead stream 252 is passed to an aromatics purification unit 260 to generate a purified aromatics stream 262, and a raffinate stream 264. The raffinate stream 264 is passed to the first reformer 210 to generate more C6 and C7 aromatics.

The light hydrocarbon fractionation unit 240 can be a debutanizer or depentanizer. The choice is controlled by operating conditions, and the extent to which the reformers 210, 220 generate butane and pentane.

The raffinate stream 264 can be passed to a hydrotreater 270 to generate a reduced sulfur raffinate stream 272, with the reduced sulfur raffinate stream 272 passed to the first reformer 210.

The process of splitting the naphtha feedstream can be further refined to take advantage of the operating conditions in the reformers. The different operating conditions in addition to temperatures, pressures, and WHSVs, can also include different catalysts as described above.

Figure 5:
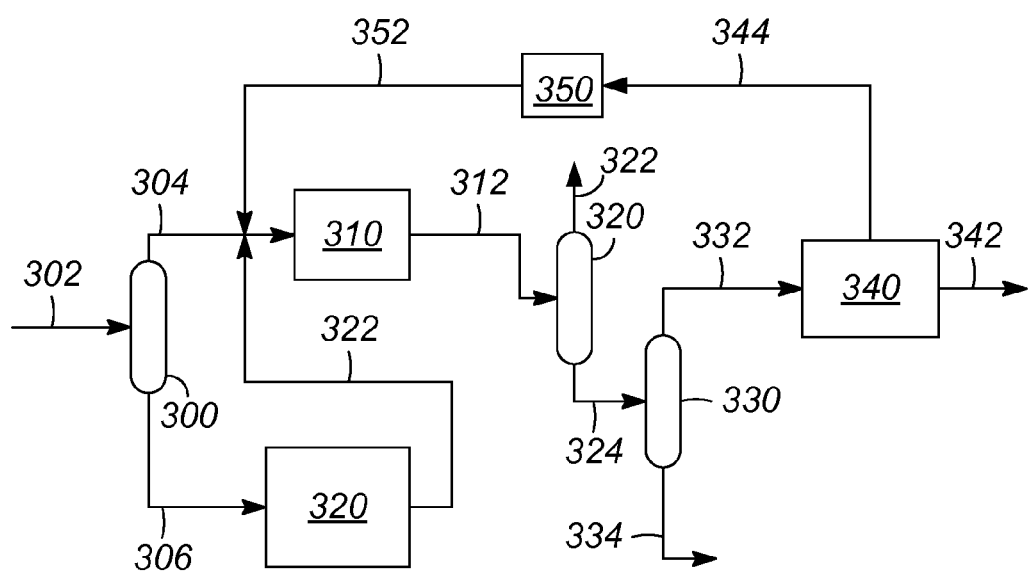
FIG. 5 is a process utilizing raffinate recycle with a series process flow of the hydrocarbon process stream.

Another split feed with recycle design is shown in FIG. 5. The process includes splitting a naphtha feedstream 302 into a light hydrocarbon stream 304 and a heavy hydrocarbon stream 306. The light hydrocarbon stream 304 is passed to a first reformer 310. The heavy hydrocarbon stream 306 is passed to a second reformer 360, which generates a second reformer effluent stream 322. The second reformer effluent stream 322 is passed to the first reformer 310. The first reformer 310 generates a first reformer effluent stream 312. The first reformer effluent stream 312 is passed to an aromatics extraction unit 340 where a purified light aromatics stream 342 is recovered. The aromatics extraction unit 340 generates a raffinate stream 344, which is recycled to the first reformer 310.

The first reformer effluent stream 310 can be separated to reduce the flow to the aromatics extraction unit 340 by removing light ends and heavy ends from the effluent stream 310. The effluent stream 310 is passed to a light hydrocarbon fractionation unit 320 which strips off a light gas stream 322 comprising hydrogen, light gases and hydrocarbons in the C1 to C5 range. The light hydrocarbon fractionation unit 320 generates a bottoms stream 324 which is passed to a reformate splitter 330. The reformate splitter 330 generates a light reformate overhead stream 332 comprising light aromatics and a heavy reformate bottoms stream 334 comprising heavy aromatics. The light reformate overhead stream 332 is passed to the aromatics extraction unit 340 where the purified aromatics stream 342 is recovered.

The reformate splitter 330 can be operated to generate a light aromatics overhead stream 332 comprising C6 to C8 aromatics, or preferably C6 and C7 aromatics, with the bottoms stream 334 comprising C9+ aromatics, or preferably C8+ aromatics and heavier hydrocarbons.

The light hydrocarbon fractionation unit 320 can be operated to be a depentanizer or a debutanizer. The operating conditions will depend on the light hydrocarbon fractionation unit feed 312 composition and the need to maintain appropriate flow conditions.

The reformers 310, 360 are operated at different sets of reaction conditions, with the first reformer 310 preferably operated at a temperature of at least 560 C. The first reformer 310 reaction conditions include a first temperature greater than the temperature of the second reformer 360. The first reformer 310 can also be operated at a lower pressure than the second reformer 360, and with shorter residence times for the reactants.

The process can also include a hydrotreater 350 for treating the raffinate stream 344. The treated raffinate stream 352, having a reduced sulfur content, is then passed to the first reformer 310. In addition, a hydrotreater can be used to treat the naphtha feedstream 302 when there are residual sulfur compounds that need to be removed before passing the naphtha feedstream 302 to the reformer 310.

The process was tested with bench scale proof of principle tests, and simulations for commercial level production of aromatics. Table 1 presents the results of the selectivity enhancements resulting from the addition of recycle of the raffinate stream.

TABLE 1

Selectivity enhancement

| Case | selectivity % | | | |
|---|---|---|---|---|
| | A6-A11+ | A6-A10 | A7-A10 | A11+ |
| Base case, A, C7– | 70.7 | 64.1 | 58.2 | 6.6 |
| Base case, B, C8– | 70.6 | 64.1 | 58.1 | 6.5 |
| C, dC5 and recycle | 77.5 | 70.9 | 63.2 | 6.6 |
| D, dC5, frac, recycle | 78.3 | 71.6 | 64.5 | 6.7 |
| E, dC4, frac, recycle | 78.4 | 71.8 | 64.6 | 6.6 |

Comparison of results for the process design shows the increase in aromatics production. The case are a base case, A, where the reformate splitter generated an overhead of C7-aromatics; a base case, B, where the reformate splitter generated an overhead of C8-aromatics; an improve case, C, with a depentanizer, without the reformate splitter, and raffinate recycle to the first reformer; an improved case, D, where the reformate splitter generated an overhead of C8-aromatics, with a depentanizer, and raffinate recycle to a second reformer; and an improved case, E, where the reformate splitter generated an overhead of C8-aromatics, with a debutanizer, and raffinate recycle to a second reformer. All of the cases, A-E, were run with an inlet temperature of 540 C (1004 F).

The feed distribution was in percent by wt. 56.67% paraffins; 31.11% naphthenes; and 12.22% aromatics. The hydrogen to hydrocarbon ratio in the reformers was 2.0, and the reformers were operated at a pressure of 446 kPa (50 psig). The catalyst was a commercial CCR catalyst having a high density and high yield.

The process translates to a substantial increase in the amount of aromatics produced. The cases are simulated for a production of aromatics with a feed of 25000 BPSD, or approximately 1087 kMTA.

TABLE 2

Commercial production increase

| | kMTA aromatics | | | | | | |
|---|---|---|---|---|---|---|---|
| Case | Total aromatics | A6 (benzene) | A7 (toluene) | A8 (xylenes) | A9 | A10 | A11+ |
| A | 765.8 | 64.5 | 160.6 | 186.6 | 161 | 122.3 | 70.82 |
| B | 764.7 | 64.5 | 160.7 | 188.1 | 161 | 122.3 | 70.8 |
| C | 842.6 | 82.9 | 187.9 | 210.3 | 165.4 | 124.1 | 72 |
| D | 851.5 | 77.7 | 194.9 | 214.4 | 167.6 | 124.5 | 72.5 |
| E | 852.8 | 78.1 | 195.3 | 214.7 | 167.7 | 124.5 | 72.5 |

The results of recycle show a significant increase in the yields with respect to the base cases. The increases are also primarily aromatics in the C6 to C8 range with much smaller increases in higher aromatics. This method provides for increasing the yields without a significant increase in lesser desired by-products.

The same set of examples were run with inlet temperatures to the reformer set to 560 C (1040 F). Simulations were performed for testing the effect of an increase in the inlet temperature to the reformers.

TABLE 3

Selectivity for inlet temperature at 560 C.

| Case | selectivity % | | | |
|---|---|---|---|---|
| | A6-A11+ | A6-A10 | A7-A10 | A11+ |
| Base case, A, C7– | 74.8 | 68.3 | 62 | 6.5 |
| Base case, B, C8– | 74.7 | 68.2 | 61.9 | 6.5 |
| C, dC5 and recycle | 77.8 | 71.3 | 63.4 | 6.5 |
| D, dC5, frac, recycle | 78.9 | 72.2 | 64.5 | 6.7 |
| E, dC4, frac, recycle | 79.2 | 72.5 | 64.5 | 6.7 |

TABLE 4

Commercial production increase at elevated inlet temperature

| | kMTA aromatics | | | | | | |
|---|---|---|---|---|---|---|---|
| Case | Total aromatics | A6 (benzene) | A7 (toluene) | A8 (xylenes) | A9 | A10 | A11+ |
| A | 810.8 | 68.8 | 178.7 | 205.1 | 165 | 122.6 | 70.6 |
| B | 812.6 | 68.8 | 178.7 | 206.9 | 165 | 122.6 | 70.6 |
| C | 846 | 85.8 | 188.3 | 212.2 | 165.6 | 123.1 | 71 |
| D | 857.9 | 84.1 | 194.7 | 213.9 | 167.3 | 125.3 | 72.6 |
| E | 860.7 | 86.6 | 194.8 | 213.9 | 167.3 | 125.3 | 72.6 |

The present invention provides for increased production of aromatics, and in particular increased benzene and toluene, from a naphtha feedstream. The process of recycle and repositioning the aromatics extraction unit relative to one or two reformers generates as much as a 25% increase in the benzene yields, and about a 10% increase in toluene yields.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for increasing aromatics production from a naphtha feedstream comprising:

passing the naphtha feedstream containing aromatic hydrocarbons, naphthenes, and more than 50 wt. % of paraffins and a hydrogen stream to a first reformer containing a reforming catalyst operated at a first set of reforming conditions to convert paraffins and naphthenes to aromatic compounds via dehydrogenation and cyclization reactions, wherein the reforming conditions include a first temperature at least 540° C., and thereby creating a first reformer effluent;

passing the first reformer effluent stream to a depentanizer or debutanizer, thereby creating a light gas stream, and a bottoms stream comprising aromatics;

passing the bottoms stream to a reformate splitter, thereby creating an overhead stream comprising C6 to C7 aromatics, and a bottoms stream comprising C8 aromatics and heavier hydrocarbon compounds;

passing the overhead stream to an aromatics separation unit, thereby creating an aromatics product stream and a raffinate stream containing paraffins and naphthenes;

passing the raffinate stream to a second reformer operated at a second set of reforming conditions to convert paraffins and naphthenes to aromatics, wherein the reforming conditions include a second temperature lower than the first temperature, and thereby creating a second reformer effluent; and passing the second reformer effluent to the depentanizer or debutanizer.

2. The process of claim 1 wherein the bottoms stream comprises at least 0.5 wt % C5 hydrocarbons compounds.

3. The process of claim 1 wherein the second temperature is greater than 540° C.

4. The process of claim 3 wherein the second temperature is greater than 550° C.

5. The process of claim 1 wherein a portion of raffinate stream is passed to the first reformer.

6. The process of claim 1 further comprising:

passing the naphtha feedstream to a hydrotreater prior, thereby creating a naphtha feedstream with a reduced sulfur content; and passing the hydrotreater effluent stream to the first reformer.

7. The process of claim 1 further comprising:

passing the naphtha feedstream to a hydrotreater prior, thereby creating a naphtha feedstream with a reduced sulfur content; and passing the raffinate stream to a hydrotreater, thereby creating a hydrotreater effluent stream; and passing the hydrotreater effluent stream to the second reformer.

* * * * *